United States Patent
McLoughlin et al.

(10) Patent No.: US 12,023,303 B2
(45) Date of Patent: Jul. 2, 2024

(54) SYSTEM FOR DETERMINING ACCURACY OF SERIALLY-CONNECTED DRUG MODULES IN A COMBINATORIAL DRUG DELIVERY DEVICE USING VOLTAGE

(71) Applicant: Bristol-Myers Squibb Company, Princeton, NJ (US)

(72) Inventors: Martin John McLoughlin, Hillsborough, NJ (US); Stephen Lawrence Zieminski, East Brunswick, NJ (US); Jeffrey Manfred Gunnarsson, Baltimore, MD (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 97 days.

(21) Appl. No.: 17/771,702

(22) PCT Filed: Nov. 2, 2020

(86) PCT No.: PCT/US2020/058499
§ 371 (c)(1),
(2) Date: Apr. 25, 2022

(87) PCT Pub. No.: WO2021/091813
PCT Pub. Date: May 14, 2021

(65) Prior Publication Data
US 2022/0378656 A1    Dec. 1, 2022

Related U.S. Application Data

(60) Provisional application No. 62/932,805, filed on Nov. 8, 2019.

(51) Int. Cl.
*A61J 1/20*    (2006.01)
*B01F 23/40*    (2022.01)
(Continued)

(52) U.S. Cl.
CPC ........... *A61J 1/2089* (2013.01); *A61J 1/2003* (2015.05); *B01F 23/49* (2022.01); *B01F 33/846* (2022.01); *G16H 20/17* (2018.01); *B01F 2101/22* (2022.01)

(58) Field of Classification Search
CPC ........ A61J 1/2089; A61J 1/2003; A61J 3/002; A61J 1/20; A61J 1/2048; A61J 1/065;
(Continued)

(56) References Cited

U.S. PATENT DOCUMENTS 6,009,344 A * 12/1999 Flower ..................... A61N 1/30
604/20
9,283,145 B2 * 3/2016 Beiriger ................ A61M 5/142
(Continued)

FOREIGN PATENT DOCUMENTS

JP    2018519141 A    7/2018
JP    2018536946 A    12/2018
(Continued)

OTHER PUBLICATIONS

International Search Report and Written Opinion of the International Searching Authority from PCT International Application No. PCT/US2020/058499, dated Mar. 9, 2021.

*Primary Examiner* — Donnell A Long
(74) *Attorney, Agent, or Firm* — Budzyn IP Law, LLC

(57) ABSTRACT

A combinatorial drug delivery device is provided herein including: a plurality of serially connectable modules, each including at least one drug component; and, a master controller. Each of the modules includes: a power line; a ground line; a multiplexer having a plurality of identified input channels, at least a subset of the input channels being selectively connected to one of the power and ground lines; a first digital logic line configured to select the input channels; a voltage reference line having a first resistor in line with an output of the multiplexer; a branch line con-
(Continued)

nected to the voltage reference line having a normally closed switch thereon to connect the branch line to the ground line, the switch being opened with connection to a further module. The master controller selects, in sequence, the same identified input channels across all of the modules with measuring a reference voltage thereacross.

5 Claims, 12 Drawing Sheets

(51) Int. Cl.
  *B01F 33/84* (2022.01)
  *G16H 20/17* (2018.01)
  *B01F 101/22* (2022.01)
(58) Field of Classification Search
  CPC ........... A61J 1/10; B01F 23/49; B01F 33/846; B01F 2101/22; G16H 20/17; A61M 5/1409; A61K 39/00
  See application file for complete search history.

(56) References Cited

U.S. PATENT DOCUMENTS

| 2017/0020784 A1 | 1/2017 | Schweiss et al. |
| 2017/0168967 A1 | 6/2017 | Mishra et al. |

FOREIGN PATENT DOCUMENTS

| WO | 2000009069 A1 | 2/2000 |
| WO | 2019217820 A1 | 11/2019 |
| WO | 2019217845 A1 | 11/2019 |
| WO | 2019217864 A1 | 11/2019 |

\* cited by examiner

| Mod 6 | Mod 5 | Mod 4 | Mod 3 | Mod 2 | Mod 1 | Vout/Vref |
|---|---|---|---|---|---|---|
| – | – | – | – | – | 1 | 0.5 |
| – | – | – | – | 1 | 1 | 0.75 |
| – | – | – | – | 1 | 0 | 0.25 |
| – | – | – | 1 | 1 | 1 | 0.875 |
| – | – | – | 1 | 1 | 0 | 0.375 |
| – | – | – | 1 | 0 | 1 | 0.625 |
| – | – | – | 1 | 0 | 0 | 0.125 |
| – | – | 1 | 1 | 1 | 1 | 0.9375 |
| – | – | 1 | 1 | 1 | 0 | 0.4375 |
| – | – | 1 | 1 | 0 | 1 | 0.6875 |
| – | – | 1 | 1 | 0 | 0 | 0.1875 |
| – | – | 1 | 0 | 1 | 1 | 0.8125 |
| – | – | 1 | 0 | 1 | 0 | 0.3125 |
| – | – | 1 | 0 | 0 | 1 | 0.5625 |
| – | – | 1 | 0 | 0 | 0 | 0.0625 |

"–" Means 0 Or No Module Connected

FIG.9

| Mod 6 | Mod 5 | Mod 4 | Mod 3 | Mod 2 | Mod 1 | Vout/Vref |
|---|---|---|---|---|---|---|
| - | 1 | 1 | 1 | 1 | 1 | 0.96875 |
| - | 1 | 1 | 1 | 1 | 0 | 0.46875 |
| - | 1 | 1 | 1 | 0 | 1 | 0.71875 |
| - | 1 | 1 | 1 | 0 | 0 | 0.21875 |
| - | 1 | 1 | 0 | 1 | 1 | 0.84375 |
| - | 1 | 1 | 0 | 1 | 0 | 0.34375 |
| - | 1 | 1 | 0 | 0 | 1 | 0.59375 |
| - | 1 | 1 | 0 | 0 | 0 | 0.09375 |
| - | 1 | 0 | 1 | 1 | 1 | 0.90625 |
| - | 1 | 0 | 1 | 1 | 0 | 0.40625 |
| - | 1 | 0 | 1 | 0 | 1 | 0.65625 |
| - | 1 | 0 | 1 | 0 | 0 | 0.15625 |
| - | 1 | 0 | 0 | 1 | 1 | 0.78125 |
| - | 1 | 0 | 0 | 1 | 0 | 0.28125 |
| - | 1 | 0 | 0 | 0 | 1 | 0.53125 |
| - | 1 | 0 | 0 | 0 | 0 | 0.03125 |

FIG.10

| Mod 6 | Mod 5 | Mod 4 | Mod 3 | Mod 2 | Mod 1 | Vout/Vref |
|---|---|---|---|---|---|---|
| 1 | 1 | 1 | 1 | 1 | 1 | 0.984375 |
| 1 | 1 | 1 | 1 | 1 | 0 | 0.484375 |
| 1 | 1 | 1 | 1 | 0 | 1 | 0.734375 |
| 1 | 1 | 1 | 1 | 0 | 0 | 0.234375 |
| 1 | 1 | 1 | 0 | 1 | 1 | 0.859375 |
| 1 | 1 | 1 | 0 | 1 | 0 | 0.359375 |
| 1 | 1 | 1 | 0 | 0 | 1 | 0.609375 |
| 1 | 1 | 1 | 0 | 0 | 0 | 0.109375 |
| 1 | 1 | 0 | 1 | 1 | 1 | 0.921875 |
| 1 | 1 | 0 | 1 | 1 | 0 | 0.421875 |
| 1 | 1 | 0 | 1 | 0 | 1 | 0.671875 |
| 1 | 1 | 0 | 1 | 0 | 0 | 0.171875 |
| 1 | 1 | 0 | 0 | 1 | 1 | 0.796875 |
| 1 | 1 | 0 | 0 | 1 | 0 | 0.296875 |
| 1 | 1 | 0 | 0 | 0 | 1 | 0.546875 |
| 1 | 1 | 0 | 0 | 0 | 0 | 0.046875 |

FIG. 11

| Mod 6 | Mod 5 | Mod 4 | Mod 3 | Mod 2 | Mod 1 | Vout/Vref |
|---|---|---|---|---|---|---|
| 1 | 0 | 1 | 1 | 1 | 1 | 0.953125 |
| 1 | 0 | 1 | 1 | 1 | 0 | 0.453125 |
| 1 | 0 | 1 | 1 | 0 | 1 | 0.703125 |
| 1 | 0 | 1 | 1 | 0 | 0 | 0.203125 |
| 1 | 0 | 1 | 0 | 1 | 1 | 0.828125 |
| 1 | 0 | 1 | 0 | 1 | 0 | 0.328125 |
| 1 | 0 | 1 | 0 | 0 | 1 | 0.578125 |
| 1 | 0 | 1 | 0 | 0 | 0 | 0.078125 |
| 1 | 0 | 0 | 1 | 1 | 1 | 0.890625 |
| 1 | 0 | 0 | 1 | 1 | 0 | 0.390625 |
| 1 | 0 | 0 | 1 | 0 | 1 | 0.640625 |
| 1 | 0 | 0 | 1 | 0 | 0 | 0.140625 |
| 1 | 0 | 0 | 0 | 1 | 1 | 0.765625 |
| 1 | 0 | 0 | 0 | 1 | 0 | 0.265625 |
| 1 | 0 | 0 | 0 | 0 | 1 | 0.515625 |
| 1 | 0 | 0 | 0 | 0 | 0 | 0.015625 |

FIG.12

SYSTEM FOR DETERMINING ACCURACY OF SERIALLY-CONNECTED DRUG MODULES IN A COMBINATORIAL DRUG DELIVERY DEVICE USING VOLTAGE

CROSS-REFERENCE TO RELATED APPLICATIONS

This application is a National Stage Application under 35 U.S.C. § 371 of PCT Application No. PCT/US2020/058499, filed Nov. 2, 2020, which claims the priority benefit of U.S. Provisional Application No. 62/932,805, filed Nov. 8, 2019; the contents of which are herein incorporated by reference in their entireties.

BACKGROUND OF THE INVENTION

Combinatorial drug delivery devices and systems are shown and described in: U.S. Provisional Patent Appl. No. 62/670,266, filed May 11, 2018; PCT Appl. No. PCT/US2019/031727, filed May 10, 2019; PCT Appl. No. PCT/US2019/031762, filed May 10, 2019; and, PCT Appl. No. PCT/US2019/031791, filed May 10, 2019. All of the aforementioned patent filings are by the same assignee as herein. As shown in the aforementioned patent filings, drug modules of different liquid drugs may be provided in various combinations to provide different (individualized) drug combinations. The drug modules may be nested, i.e., connected, in series or in parallel, on a tray or other base structure. Alternatively, the drug modules may be serially connected (vertically and/or horizontally) directly to one another. U.S. Provisional Patent Appl. No. 62/670,266, PCT Appl. No. PCT/US2019/031727, PCT Appl. No. PCT/US2019/031762, and, PCT Appl. No. PCT/US2019/031791, are incorporated by reference herein in their respective entireties.

The serially-connected combinatorial system has the advantage in comparison with the nested designs in that it does not require a separate tray component to make the fluid connections and is therefore more efficient in components and, thus, in supply chain.

In the nested system, the tray design can 'store' information on the correct configuration of the modules through the inherent design and layout of the tray design. For example, the tray may provide a configuration (e.g., mechanical cooperating features, such as "lock and key" features) that guarantee only the correct drug modules can be inserted into the nests of the tray and that the correct drug modules are arranged in the correct order. This acts as a safety check in preparing the drug modules for use. In contrast, the serially-connected system does not have a tray-type element and, thus, lacks the ability to have a safety check on this basis.

Because tray-based mechanical means of error prevention are not possible in the serially-connected case, it is desirable to implement other means of detecting configuration errors in the serially-connected system and hence prevent the occurrence of medication errors.

SUMMARY OF THE INVENTION

A combinatorial drug delivery device is provided herein including: a plurality of serially connectable modules, each of the modules including at least one drug component; and, a master controller having a source of power and a ground. Each of the modules includes: a power line, wherein, with the modules being serially connected, the power lines are connected in series between the modules with the serially connected power lines being connected to the source of power; a ground line, wherein, with the modules being serially connected, the ground lines are connected in series between the modules with the serially connected ground lines being connected to the ground; a multiplexer having a plurality of identified input channels and a single output, wherein at least a subset of the input channels is selectively connected to one of the power line and the ground line of the corresponding module; a first digital logic line configured to select the input channels, wherein, with the modules being serially connected, the first digital logic lines are connected in series between the modules with the serially connected first logic lines being connected to the master controller; a voltage reference line having a first resistor of known value in line with the output of the multiplexer, and a second resistor of known value in parallel to the first resistor, wherein, with the modules being serially connected, the voltage reference lines are connected in series between the modules with the serially connected voltage reference lines being connected to the master controller; a branch line connected to the voltage reference line having a third resistor of known value and a normally closed switch thereon to connect the branch line to the ground line, the switch being opened with connection to a further module. The master controller, using the first digital logic line, selects, in sequence, the same identified input channels across all of the modules with measuring a reference voltage across all of the modules for each of the same identified input channels. Advantageously, the measured reference voltages may be used to identify binary codes associated with the modules, thus, providing indication of the contents of each module and the sequence of the modules.

These and other features of the invention will be better understood through a study of the detailed description and accompanying drawings.

BRIEF DESCRIPTION OF THE DRAWINGS

FIGS. 1-13B depict various features of a device formed in accordance with the subject invention.

DETAILED DESCRIPTION OF THE INVENTION

Figure 1:
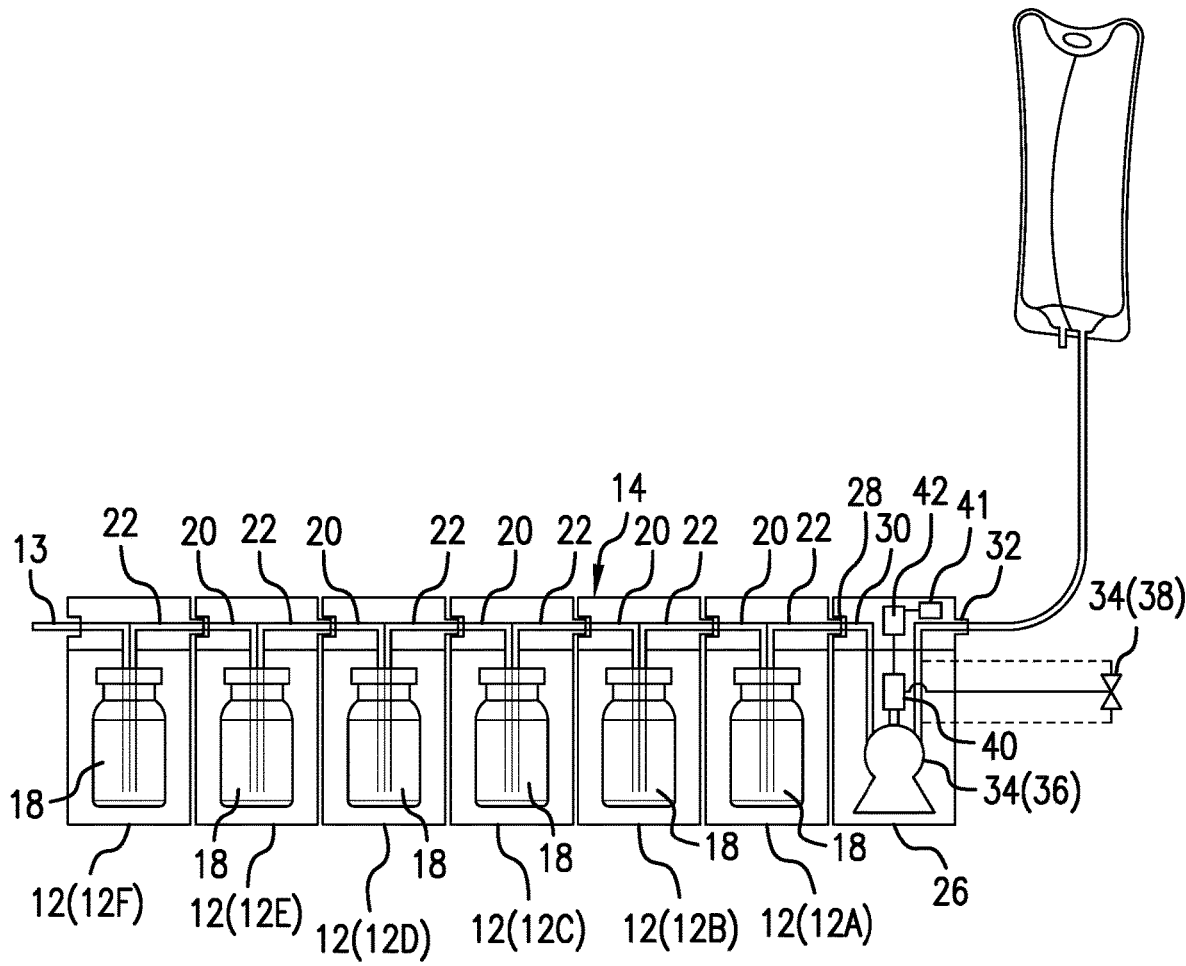
Figure 2:
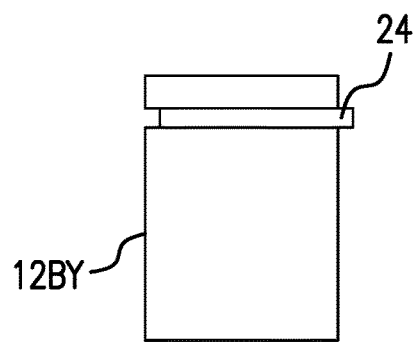
Figure 3:
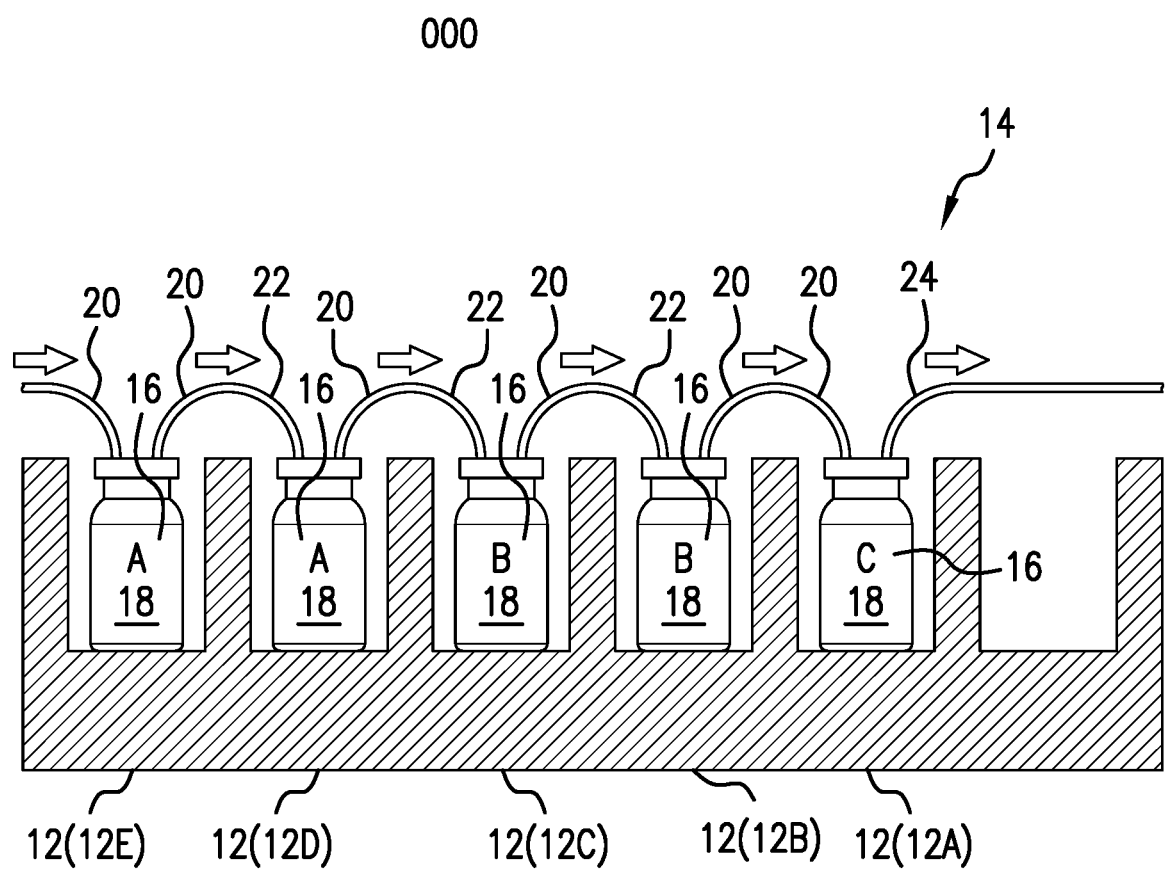

With reference to FIGS. 1-3, an arrangement is shown useable to verify the accuracy of a plurality of serially-connected drug modules 12 of a combinatorial drug delivery device 14. Each of the drug modules 12 includes a drug reservoir 16 for accommodating a liquid drug 18. The drug reservoirs 16 may be defined by portions of the drug modules 12, or be defined by components, such as vials, inserted into the drug modules 12. The combinatorial drug delivery device 14, including any aspect thereof, may be formed in accordance with any of the embodiments disclosed in any of U.S. Provisional Patent Appl. No. 62/670,266, PCT Appl. No. PCT/US2019/031727, PCT Appl. No. PCT/US2019/031762, and, PCT Appl. No. PCT/US2019/031791. For illustrative purposes, exemplary features of the combinatorial drug delivery device 14 are described herein. As will be recognized by those skilled in the art, the subject invention is useable with any of the combinatorial drug delivery devices, including being useable with any of the elements thereof (e.g., system 10, drug modules 12, manner of connecting the drug modules 12, flow controller 34, etc.), disclosed in any of the aforementioned patent filings.

As shown in FIG. 1, the drug modules 12 are serially-connected so as to define a single flow path for the drug delivery device 14 through the series of the drug modules 12, through which the liquid drug 18 of each of the drug modules 12 may be drawn. As shown in FIG. 1, inlet and outlet tubing 20, 22, may be provided for each of the drug modules 12 so that the liquid drug 18 may be drawn, in succession, from each of the drug modules 12. As shown in FIG. 3, the inlet and outlet tubing 20, 22 may be formed continuously between the drug reservoirs 16 so that lengths of tubing are provided serving both as an outlet of one of the drug reservoirs 16 and an inlet for the next drug reservoir 16. FIG. 1 shows six of the drug modules 12 (12A-12F). As will be appreciated by those skilled in the art, any quantity of the drug modules 12 may be utilized. A vent 13 may be provided at a terminus of the flow path (in the ultimate drug module).

It is noted that one or more by-pass drug modules 12BY may be needed in a series, to accommodate a place in the series, but to not contain any liquid drug. As shown in FIG. 2, the by-pass drug module 12BY may have by-pass tubing 24 which extends from the inlet to the outlet thereof to allow for flow therethrough without a drug reservoir. Alternatively, as shown in FIG. 3, the by-pass tubing 24 may be provided in lieu of one of the drug modules 12 to connect two components of the drug delivery device 14, such as two of the drug modules 12 or one of the drug modules 12 and the controller housing described below.

The liquid drugs 18 contained in the drug modules 12 may vary in type and concentration. The liquid drug 18 in some of the modules 12 may be a diluent with no pharmaceutically or biologically active agents. The drug modules 12 may contain one or more solid components which can be reconstituted with flow of a diluent therein to form a liquid drug. The ability of the serially-connected drug modules 12 to contain various drug types and concentrations allows for the drug delivery device 14 to be a combinatorial drug delivery device 14, providing for the mixing of various liquid drugs. The liquid drugs 18 intended for a particular combination for a patient is prescribed by a physician. The subject invention provides for the confirmation of accuracy of the inclusion of the particular drug modules 12 in the drug delivery device 14, as well as, the sequence of the drug modules 12. The sequence of the drug modules 14 may be significant, possibly having an impact on the efficacy of the ultimate resulting combination.

The drug delivery device 14 preferably includes a controller housing 26 to which the serially-connected drug modules 12 are connected. The outlet tubing 22 of the first drug module 12A (being the closest to the controller housing 26) is in communication with an inlet 28 formed in the controller housing 26 into which the liquid drug 18 may flow from the drug modules 12. Delivery tubing 30 extends from the inlet 28 to convey the liquid drug 18 through the controller housing 26 to an outlet 32. Tubing or conveyances may be secured to the outlet 32 to direct the liquid drug 18 to a storage device (e.g., an IV bag, injector) or to a drug delivery device connected to a patient (e.g., a butterfly needle).

A flow controller 34 is provided in the controller housing 26 which selectively regulates flow through the delivery tubing 30. In one embodiment, the flow controller 34 may include an actuatable source of negative pressure 36, such as a pump, provided in the controller housing 26 to draw the liquid drug 18 through the inlet 28 and discharge the liquid drug 18 through the outlet 32, via the delivery tubing 30 (which may be discontinuous). In a quiescent state, the source of negative pressure 36 generates no negative pressure, thus, not drawing the liquid drug 18. In a further embodiment, the flow controller 34 may include one or more adjustable valves 38 provided in the controller housing 26 configured to selectively regulate flow through the delivery tubing 30, particularly being configured to be selectively adjusted between open and closed states, such as a ball valve. With the use of the valves 38, a source of negative pressure external to the controller housing 26 may be utilized which is configured to apply negative pressure to the outlet 32 to draw the liquid drug 18 therefrom.

A control unit 40 may be provided in the controller housing 26 which includes a computing processing unit (CPU) 42. It is preferred that the flow controller 34 be electrically powered to be controlled by the CPU 42. For example, an electrical motor or actuator may be provided having a switch configured to be controlled by the CPU 42. Actuation of the motor can cause the source of negative pressure 30 to be activated (e.g., the pump to be turned on), whereas, actuation of the actuator can cause adjustment of the valve(s) 38 to an open state (e.g., rotation of the valve stem to an open state). The switch may be adjusted to an off position by the CPU 42 to turn off the motor, or close the valve(s).

It is envisioned that the drug modules 12 will be serially-connected, when ready for use. Thus, assembly of the drug modules 12 is required by a user, or on behalf of a user. As a fail-safe mechanism, to ensure that the drug modules 12 are properly included in the drug delivery device 14 and in the correct sequence, each of the drug modules 12 may have circuitry therein representative of the drugs 18 contained in the drug modules 12. The circuitry may be a plurality of binary input channels of a multiplexer, the powered/grounded state of the input channels defining individual binary units which may be grouped together to provide each module with a string of binary units. The string of binary units may designate a drug type and, possibly, a drug's concentration or strength. The liquid drug 18 may be loaded into the drug modules 12 in a manufacturing facility or in a pharmacy with the input channels being adjusted to on/off (powered/grounded positions) on the modules 12 at the same time. Care is needed to configure the input channels in the drug modules 12.

The specific liquid drugs 18 (type, concentration) will be specified by prescription. The drug modules 12 will be prepared to accommodate the specified liquid drugs 18—the number of the drug modules 12 to be utilized being at least equal to the number of drug components specified by the prescription. The drug modules 12, along with the controller housing 26, may be delivered to the user or a location associated with the user as a kit, for assembly. Instructions will be provided with regards to the assembly of the drug modules 12, including the sequence of the drug modules 12, e.g., first position (closest to the controller housing 26), second position, and so forth.

Figure 4:
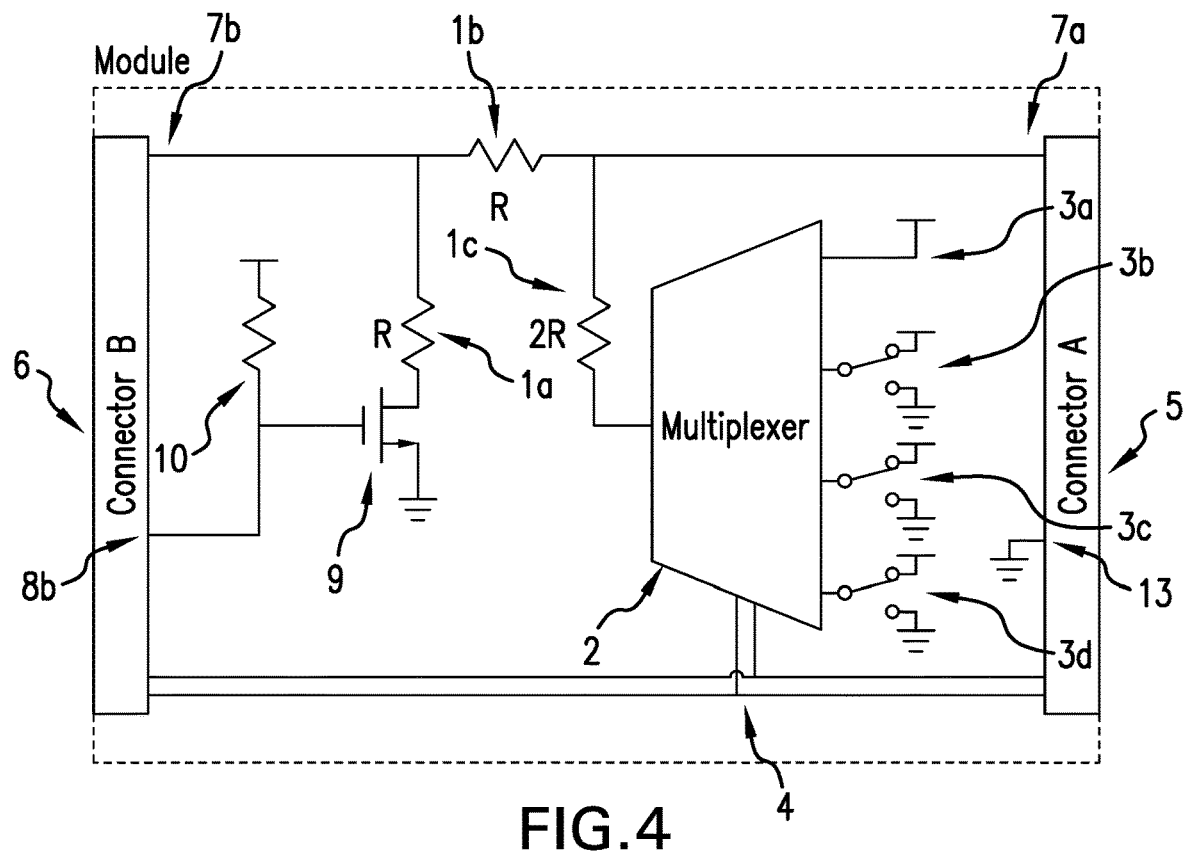
Figure 5:
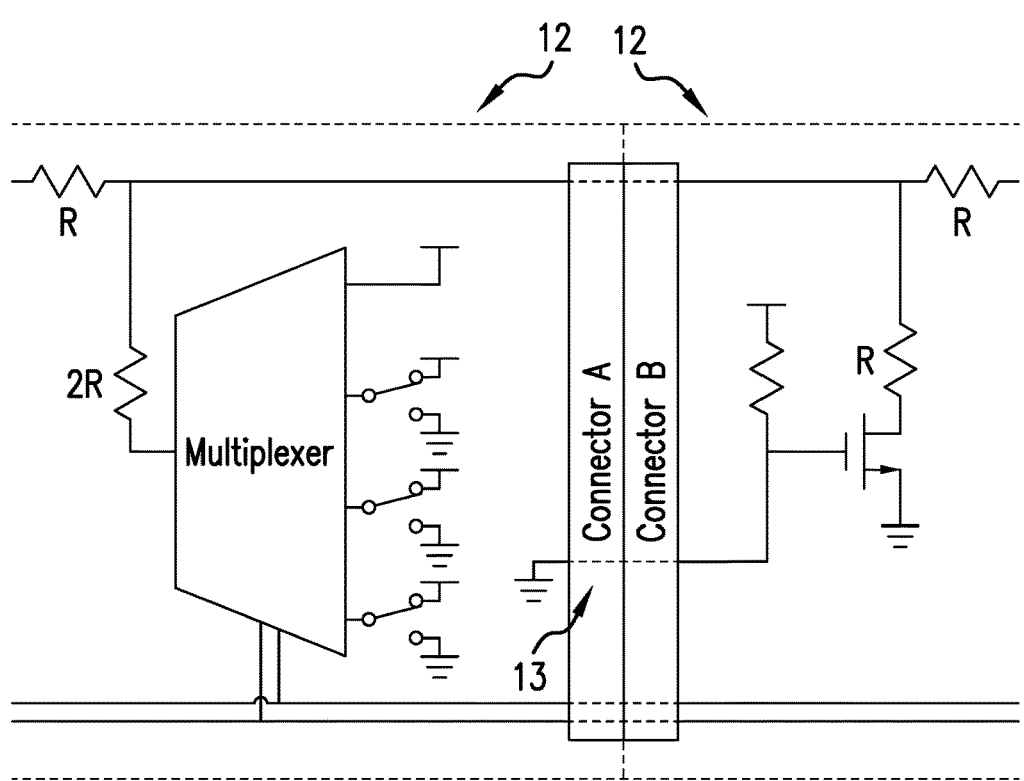
Figure 6:
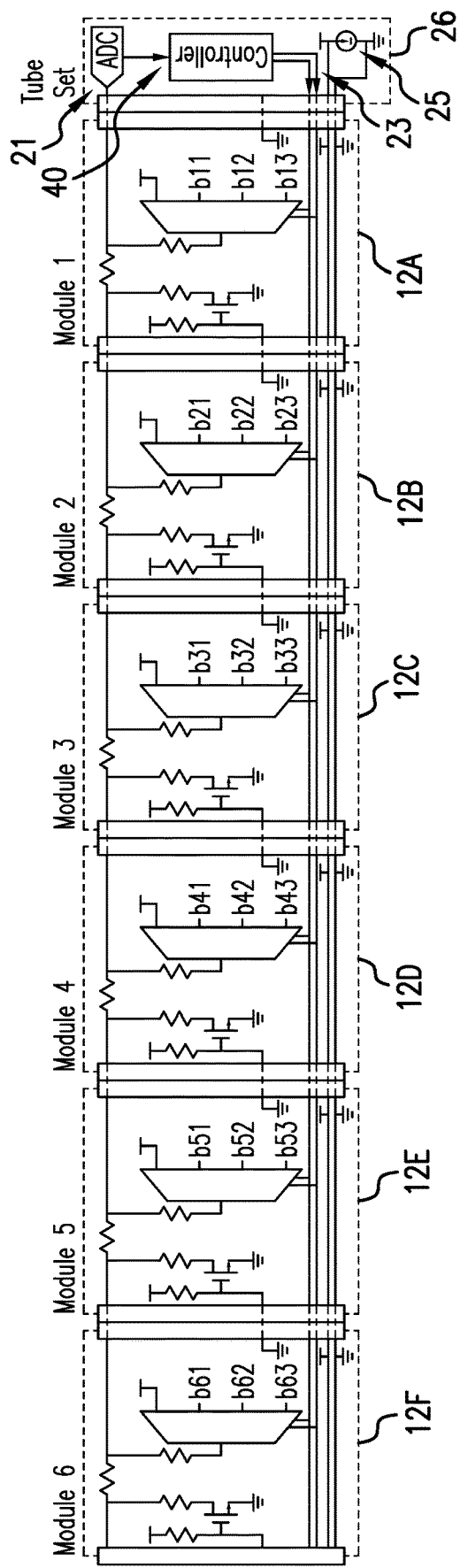

With reference to FIGS. 4-6, each of the modules 12 is provided with three resistors 1a, 1b, 1c with known values. Preferably, the resistor 1c (labeled as the 2R resistor) has a resistance value twice that of the resistors 1a, 1b (labeled as the R resistors). One side of the resistor 1c is connected to the output of an analog multiplexer 2, which connects one of several input channels 3a, 3b, 3c, 3d to a single output. The desired channel 3a, 3b, 3c, 3d is selected by one or more digital logic lines 4. In this application, the multiplexer 2 passes a voltage through from one of four input channels 3a, 3b, 3c, 3d. One of these input channels (3a) may be connected to power, while the remaining channels 3b, 3c, 3d are connected to either power or ground via a switch. These switches are configured to the string of binary units representative of the liquid drug 18 of the corresponding module 12. The switches may be in the form of, one or more of: hardware jumpers, resistor shorts, or small SPDT switches.

FIGS. 4-6 show three switches, but more are possible. The formula below relates the number of possible unique drug IDs (D) (i.e., strings of binary units) that can be configured based on the number of multiplexer channels (N):

$$D = 2^{N-1}.$$

The exponent of N−1 is used to account for the fact that one input channel of the multiplexer 2, in a preferred embodiment, may be connected directly to power rather than a switch. As discussed below, this allows for the determination of the number of modules 12 serially connected, without prior notification.

The multiplexer is controlled by at least one binary logic line 4. Each binary combination of the logic state of the logic line 4 denotes which of the multiplexer 2 input channels 3b, 3c, 3d should be passed to the multiplexer 2 output. The number of multiplexer select lines (S) (i.e., the logic lines 4) is related to the number of channels (N) by:

$$N = 2^S.$$

In FIGS. 4-6, the S=2 select lines (logic lines 4) correspond to $2^2 = 4$ multiplexer channels 3a, 3b, 3c, 3d, but this value can be doubled for each additional select line. This relationship means that the number of possible unique drug IDs is related to the number of select lines via the formula:

$$D = 2\hat{\ }[(2\hat{\ }S) - 1].$$

This relation demonstrates that with the addition of a few select lines, a virtually limitless number of drug IDs can be encoded. Table 1 below illustrates this concept. The switches 3b, 3c, 3d can take the form of resistor shorts or breakable copper traces, both of which are cheap and low-profile, meaning that switch counts of 15 or 31 are cost achievable.

TABLE 1

| Select lines | Binary switches | Drug IDs |
|---|---|---|
| 2 | 3 | 8 |
| 3 | 7 | 128 |
| 4 | 15 | 32,768 |
| 5 | 31 | >2 billion |

With the modules 12 being serially connected, an analog voltage may be generated by their combined resistor network which corresponds to the binary code of each module. When the modules 12 are connected, their mating connectors form the connections shown in FIG. 5.

The module 12A closest to the controller housing 26 plugs into operative communication with the control unit 40. As shown in FIG. 6, the control unit 40 provides power 25 and ground to the module 12A. The next module 12B plugs into the first module 12A such that the first module's 12A Connector B mates with the second module's 12B Connector A. The first module 12A then passes power through to the second module. This connectivity scheme continues such that power from the control unit 40 is connected through to all serially connected modules 12. Likewise, the multiplexer select lines 4 are passed through to all modules 12, such that the control unit 40 can globally select which multiplexer channel 3a, 3b, 3c, or 3d of each of the modules 12 is passed through to the output of each module's multiplexer 2. The select lines 4 are operatively linked to the control unit 40 through lines 23.

Figure 13A:
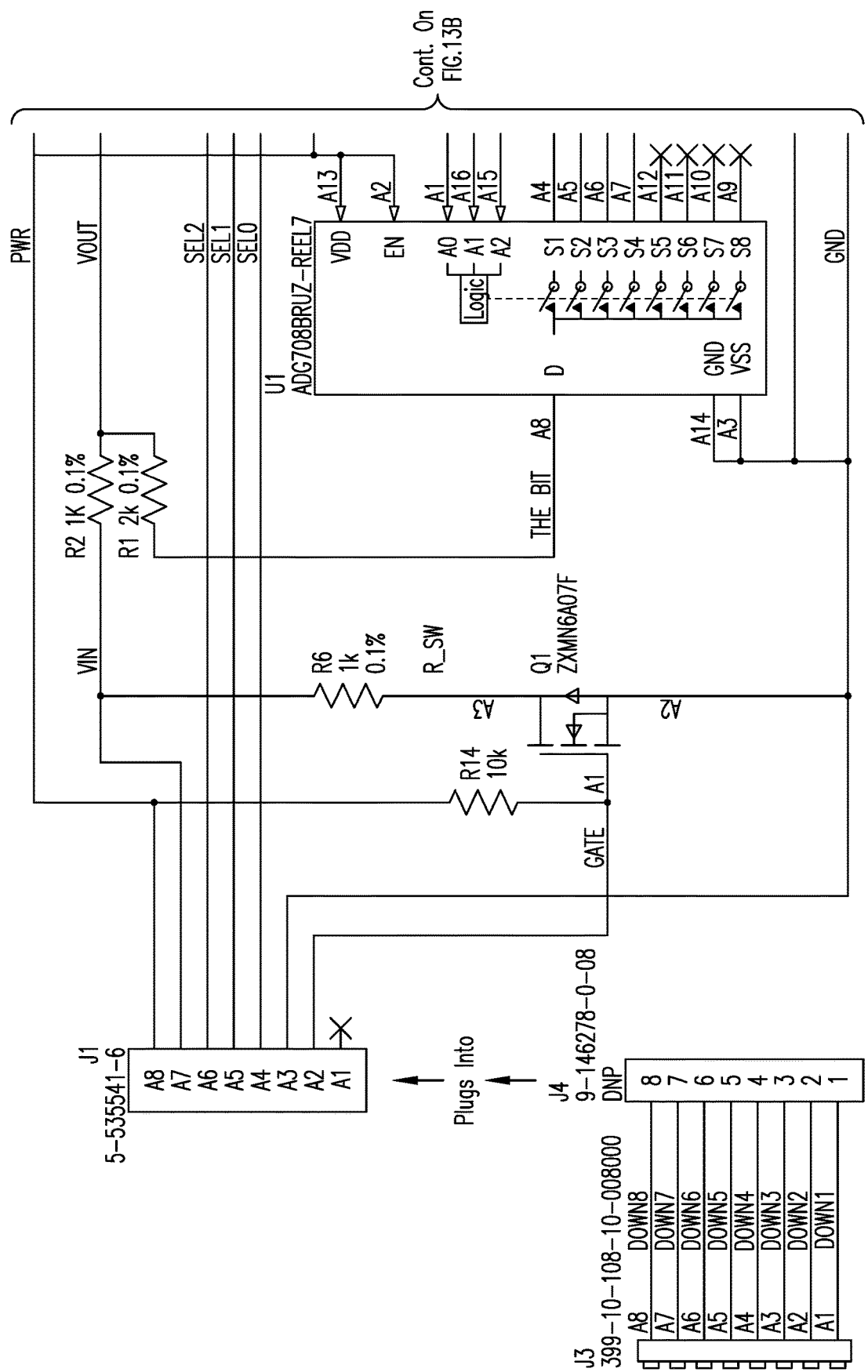
Figure 13B:
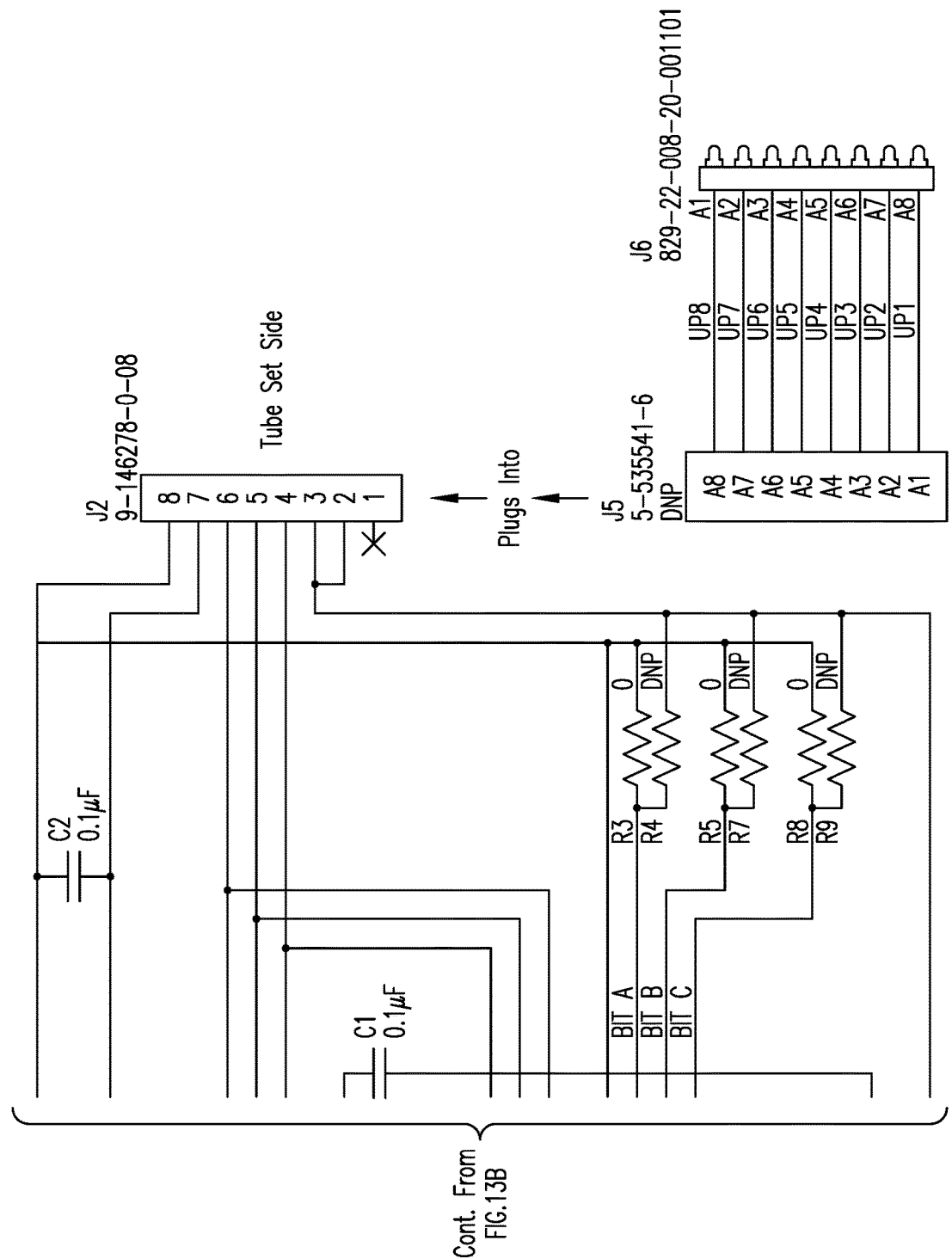

Once powered and connected, each of the modules 12 configures an analog resistor network whose output is passed through Connector A connections to the next module 12. Conversely, each of the modules 12 accepts an analog input from the previous module 12 through the corresponding Connector B connection. The resistor networks of all serially connected modules 12 combine to form an analog voltage at the output connection of the first module 12A, such that electronics in the controller housing 26 can read the analog voltage using a standard analog-to-digital converter (ADC) 21. As shown in FIGS. 13A and 13B, connectors A and B may be 8-pin socket connectors.

The resistor connection scheme is based on electrical architecture often called an R-2R resistor ladder. In order for this circuit to function, the last module in the chain must terminate the ladder to ground through an additional resistor 1a. When a given module 12 has no downstream module connected (e.g., 12F), its terminating resistor 1a is pulled to ground through an n-channel MOSFET 9, which acts as an electronic switch. The MOSFET 9 is held on by a pullup resistor 10 to power. When another module 12 is connected, that second module 12 shorts this MOSFET's gate to ground through a Connector A connection to ground 13, thus disconnecting the first module's terminating resistor 1a from ground. The new module now implements the terminating resistor 1a by virtue of the fact that it has no downstream modules connected to it.

As discussed above, the control unit 40 can select any of the N multiplexer input channels 3a, 3b, 3c, 3d by setting a binary code on the S select lines 4. For a given binary code s, the analog voltage Vout(s) generated by the M modules can be calculated. Let bms represent the binary value indicating whether or not a switch on multiplexer channel s is connected to power (bms=1) or ground (bms=0) and let Vref represent the reference voltage:

$$V_{out(s)} = V_{ref} \sum_{m=1}^{M} b_{ms} 2^{-3}.$$

For example, if M=6 modules are connected together, with the switch on their multiplexer channels configured to 1, 0, 0, 1, 0, and 1, the analog output voltage will be 0.578125 times the reference voltage. A different voltage value can be obtained for each multiplexer select code s, allowing the control unit 40 to cycle through all N multiplexer inputs.

In addition to the module count, the number of bits worth of information encoded by this scheme is equal to M(N−1). For the values of M=6 and N=4, for example, the scheme encodes a total of 262,144 permutations of drug ID (from 0 to 7) and module positions (from 1 to 6) of the drugs. Increasing the select line count from S=2 to S=3 (and thus the multiplexer channel count from N=4 to N=8) increases the range of drug IDs to 0 to 127, and the total permutation count to over 4 trillion.

Note however that the output voltage formula above requires the control unit 40 to know the module count, M In an alternate embodiment, the electronics can self-determine the number of the modules 12 by dedicating one multiplexer input (e.g., 3a) on each module 12 to power. In this way, when that multiplexer channel is selected, the output voltage $V_{count}$ corresponds to the module count and will be equal to:

$$V_{count} = V_{ref} \sum_{m=1}^{M} \frac{1}{2}.$$

For example, if the control unit 40 reads a voltage of 0.875 times the reference voltage, it can determine that the connected module count is 3, since ½+¼+⅛=0.875. Similarly, a module count of 6 yields a voltage of 0.984375 times the reference voltage.

FIG. 6 shows a full stackup of 6 modules 12 with control electronics in the controller housing 26. The control unit 40 has a power source 25, such as a battery, which is passed through to all serially connected modules 12. The control unit 40, which could be a microcontroller, CPLD, or FPGA running embedded firmware, sets the multiplexer channel select lines 23 to a given value, which is then transmitted through the select lines 4, then reads the resulting analog voltage from the modules through an analog/digital converter (ADC) 21. The control unit 40 then updates the multiplexer channel select lines 23 to the next binary value, reading the next analog voltage, and continues until one analog voltage has been obtained for each multiplexer channel 3a, 3b, 3c, 3d across all modules 12. From these voltages, the control unit 40 can use the relationships above for $V_{out(s)}$ and $V_{count}$ to determine the number of connected modules 12 and the binary drug IDs (in FIG. 6: b11, b12, b13 for Module 1; b21, b22, 23 for Module 2, etc.) of each module 12.

Figure 7:
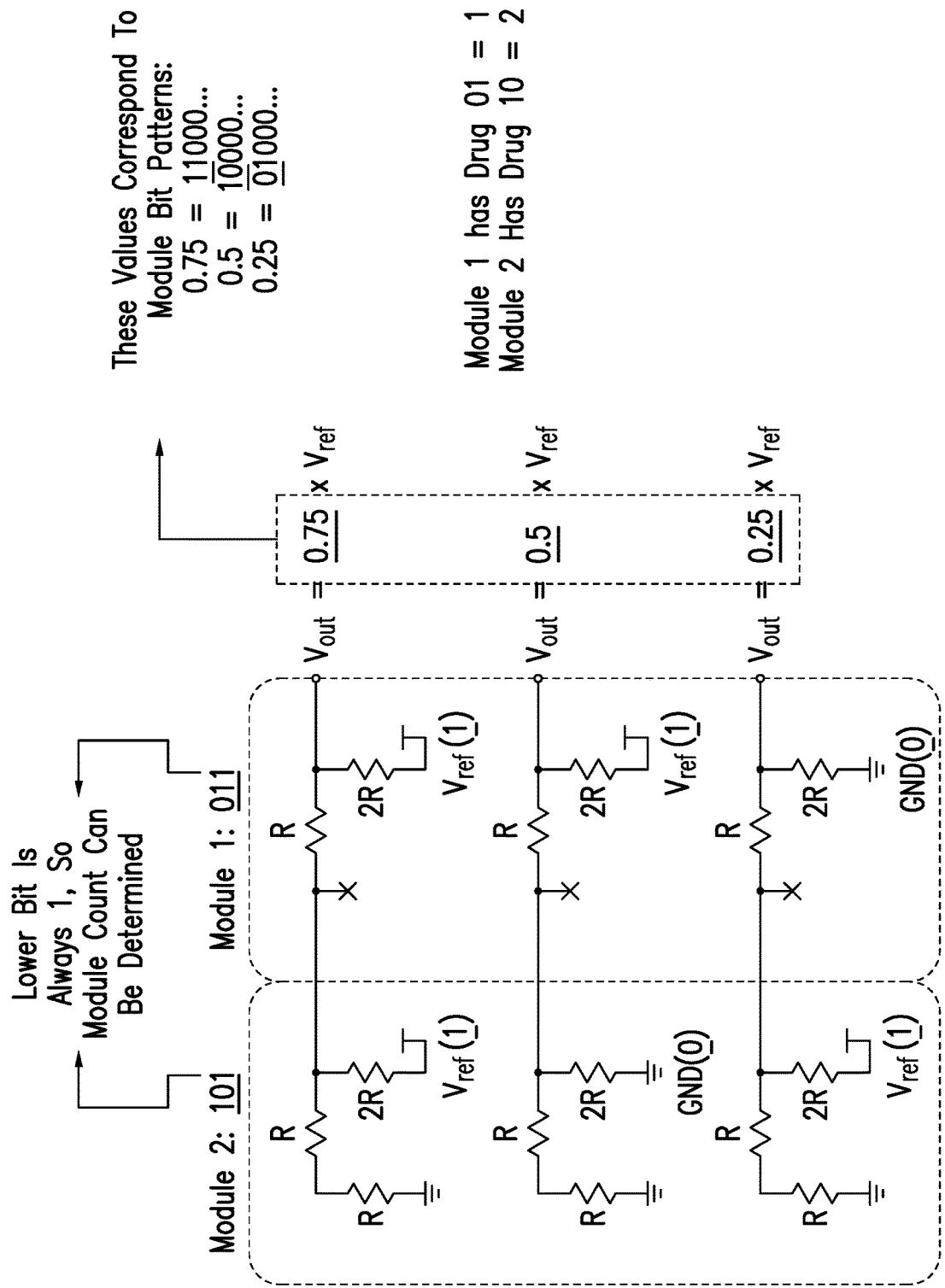
Figure 8:
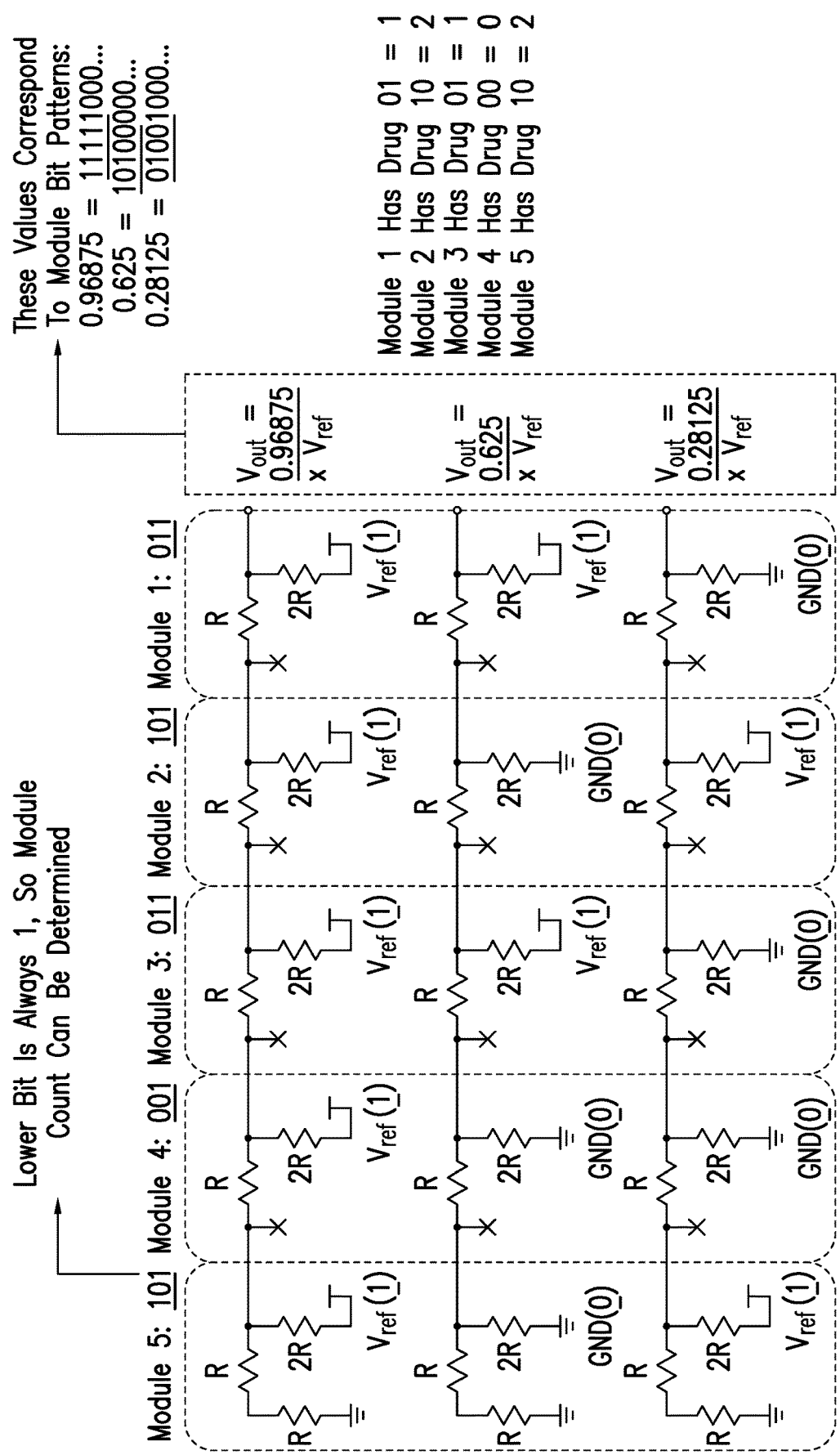

FIGS. 7-8 show different reference voltages representing different binary code readings for different input channels of the multiplexers 2 of the modules 12. For example, in FIG. 7, in the top row, a Vout=0.75*Vref is shown which represents a string of binary units beginning with 11, corresponding to both modules at this input channel having powered states. In contrast, in the second row, the left module has a grounded input channel, with the right module having a powered input channel, yielding a 10 binary reading. The bottom row has powered and grounded states opposite to the second row, and thus yields a 01 reading. With arranging these readings, the string of binary units for the left module reads 101 (bottom to top) and the right module as 011. Thus, the string of binary units for each of the modules 12 may be identified along with the sequencing of the modules 12. FIG. 8 provides a five-module illustration of the same working principle.

FIGS. 9-12 provide useable voltage ratios as indicators of different strings of binary units. By measuring the analog voltages as discussed above, a string of binary units for each of the input channels may be determined and then combined to discern drug ID's and sequencing for each of the modules 12.

FIGS. 13A and 13B show a possible printed circuit board (PCB) circuit arrangement useable in each of the modules 12.

The strings of binary units for each of the modules 12 may be placed in sequence to generate an activation code. The activation code may be used for comparison against an authentication code to determine its accuracy. In one embodiment, the authentication code may be stored in a non-transitory memory 41 associated with the CPU 42 in the controller housing 26. Alternatively, the authentication code may be transmitted to the CPU 42 (e.g., via a receiver on the controller housing 26) with the CPU 42 running a comparison to determine a match. With a match between the activation code and the authentication code, the CPU 42 may actuate the flow controller 34 to enable the delivery of the liquid drug 18.

The flow controller 34 may be provided to have a storage (i.e., non-use) state, e.g., where one or more of the adjustable valves 38 are in closed positions to not permit flow through the delivery tubing 30 to the outlet 32. In addition, or alternatively, in the storage state, the source of negative pressure 36 is in a quiescent state. With a match of the activation code and the authentication code, as described above, the CPU 42 may actuate the flow controller 34, thus causing the flow controller 34 to enter a use state. With the flow controller 34 in a use state, delivery of the liquid drug 18 from the drug delivery device 14 may be achieved. In particular, the one or more adjustable valves 38 may be adjusted to open positions to permit flow through the delivery tubing 30 to the outlet 32. In addition, the source of negative pressure 36 may be actuated, or, alternatively, may be placed into an active state, awaiting actuation (e.g., by a switch on the controller housing 26).

In one embodiment, any of the combinatorial drug delivery devices disclosed herein is able to deliver two or more drugs for the benefit of the patient suffering from any of a wide range of diseases or conditions, e.g., cancer, autoimmune disorder, inflammatory disorder, cardiovascular disease or fibrotic disorder. In one embodiment, one or more of drug modules 12 may contain a single drug. In one embodiment, one or more of drug module 12 may contain two or more co-formulated drugs. In one embodiment, one or more of drug module 12 may contain a drug in solid form (such as a tablet, capsule, powder, lyophilized, spray dried), which can be reconstituted with flow of a diluent therein to form a liquid drug.

In one embodiment, one or more of the drugs of any of the combinatorial drug delivery devices disclosed herein is an immune checkpoint inhibitor. In certain embodiments, the immune checkpoint inhibitor is Programmed Death-1 ("PD-1") pathway inhibitor, a cytotoxic T-lymphocyte-associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("IDO1") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, any of the combinatorial drug delivery devices disclosed herein includes a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, any of the combinatorial drug delivery devices disclosed herein includes a LAG3 antagonist, e.g., relatlimab or MK-4280, and a PD-1 pathway inhibitor, e.g., nivolumab (OPDIVO) or pembrolizumab (KEYTRUDA). In one embodiment, any of the combinatorial drug delivery devices disclosed herein includes a LAG3 antagonist, e.g., relatlimab or MK-4280, and a CTLA-4 antagonist, e.g., ipilimumab (YERVOY). In one embodiment, any of the combinatorial drug delivery devices disclosed herein includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDO1 antagonist. In another embodiment, the IDO1 antagonist is indoximod (NLG8189; 1-methyl-$_D$-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2',5'-3', 5' cyclic-di-nucleotides; 2'-fluoro substituted, bis-3',5' cyclic-di-nucleotides; 2',2"-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cerguutuzumab amunaleukin (RG7813, RO-6895882) or RG7802 (RO6958688).

In one embodiment, the immune checkpoint inhibitor is a CD47 antagonist. In certain embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of any of the combinatorial drug delivery devices disclosed herein is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+ T lymphocyte); CD28CAR/CD137CAR-expressing T lymphocyte; allogeneic CD4+ memory Th1-like T cells/microparticle-bound anti-CD3/anti-CD28; anti-CD19/CD28/CD3zeta CAR gammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of any of the combinatorial drug delivery devices disclosed herein is an anti-CD73 antibody or antigen binding fragment thereof. In certain embodiments, the anti-CD73 antibody is MEDI9447.

In one embodiment, one or more of the drugs of any of the combinatorial drug delivery devices disclosed herein is a TLR9 agonist. In one embodiment, the TLR9 agonist is agatolimod sodium.

In one embodiment, one or more of the drugs of any of the combinatorial drug delivery devices disclosed herein is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of any of the combinatorial drug delivery devices disclosed herein is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-beta-resistant LMP-specific cytotoxic T-lymphocytes.

In one embodiment, one or more of the drugs of any of the combinatorial drug delivery devices disclosed herein is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of any of the combinatorial drug delivery devices disclosed herein is a SHP-1 antagonist.

In one embodiment, one or more of the drugs of any of the combinatorial drug delivery devices disclosed herein is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of any of the combinatorial drug delivery devices disclosed herein is an agonist of a TNF family member. In some embodiments, the agonist of the TNF family member is ATOR 1016, ABBV-621, or Adalimumab.

In one embodiment, one or more of the drugs of any of the combinatorial drug delivery devices disclosed herein is an Interleukin-2 (IL-2), such as aldesleukin. Preferably, the IL-2 or conjugated IL-2 (e.g., pegylated) has been modified to selectively activate T-effector cells over T-regulatory cells ("T-eff IL-2"), such as bempegaldesleukin. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA). In one embodiment, any of the combinatorial drug delivery devices disclosed herein includes a modified IL-2, such as bempegaldesleukin, which selectively activates T-effector cells over T-regulatory cells, and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a CTLA-4 antagonist, e.g., ipilimumab (YERVOY), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), a CTLA-4 antagonist, e.g., ipilimumab (YERVOY), and a LAG3 antagonist, e.g., relatlimab or MK-4280.

In one embodiment, one or more of the drugs of any of the combinatorial drug delivery devices disclosed herein is a CD160 (NK1) agonist. In certain embodiments, the CD160 (NK1) agonist is an anti-CD160 antibody or antigen binding fragment thereof. In one embodiment, the anti-CD160 antibody is BY55.

In one embodiment, the one or more of drug module 12 may contain a soluble CTLA-4 polypeptide, which can be useful for treating, for instance, T-cell mediated autoimmune disorders, such as rheumatoid arthritis, juvenile idiopathic arthritis, psoriatic arthritis, graft-versus-host disease, and transplant rejection. In one embodiment, the soluble CTLA-4 polypeptide is abatacept (ORENCIA), belatacept (NULOJIX), RG2077, or RG-1046. In certain embodiments, one or more drug modules 12 of a combinatorial drug delivery device as described herein include a soluble CTLA-4 polypeptide, e.g., abatacept (ORENCIA) and a Bruton's tyrosine kinase inhibitor, e.g., branebrutinib. In certain embodiments, one or more drug modules 12 of a combinatorial drug delivery device as described herein include a soluble CTLA-4 polypeptide, e.g., abatacept (ORENCIA) and a tyrosine kinase-2 inhibitor, e.g., BMS-986165. In certain embodiments, one or more drug modules 12 of a combinatorial drug delivery device as described herein include a soluble CTLA-4 polypeptide, e.g., abatacept (ORENCIA) and an Interleukin-2 (IL-2) or "T-reg IL-2", which selectively activates T-regulatory cells as opposed to T-effector cells, e.g., BMS-986326 and NKTR-358.

What is claimed is:
1. A combinatorial drug delivery device comprising:
a plurality of serially connectable modules, each of the modules including at least one drug component; and,
a master controller having a source of power and a ground,
wherein, each of the modules includes:
a power line, wherein, with the modules being serially connected, the power lines are connected in series between the modules with the serially connected power lines being connected to the source of power;
a ground line, wherein, with the modules being serially connected, the ground lines are connected in series between the modules with the serially connected ground lines being connected to the ground;
a multiplexer having a plurality of identified input channels and a single output, wherein at least a subset of the input channels is selectively connected to one of the power line and the ground line of the corresponding module;
a first digital logic line configured to select the input channels, wherein, with the modules being serially connected, the first digital logic lines are connected in series between the modules with the serially connected first logic lines being connected to the master controller;
a voltage reference line having a first resistor of known value in line with the output of the multiplexer, and a second resistor of known value in parallel to the first resistor, wherein, with the modules being serially connected, the voltage reference lines are connected in series between the modules with the serially connected voltage reference lines being connected to the master controller;

a branch line connected to the voltage reference line having a third resistor of known value and a normally closed switch thereon to connect the branch line to the ground line, the switch being opened with connection to a further module;

wherein, the master controller, using the first digital logic line, selects, in sequence, the same identified input channels across all of the modules with measuring a reference voltage across all of the modules for each of the same identified input channels.

2. A combinatorial drug delivery device as in claim 1, wherein the switch is a n-channel MOSFET.

3. A combinatorial drug delivery device as in claim 2, wherein each of the modules includes a secondary branch line, the secondary branch being connected to the power line and a gate of the MOSFET of the corresponding module, a fourth resistor being located on the secondary branch line between the power line and the gate of the MOSFET, wherein, the secondary branch line conveys power to maintain the gate of the MOSFET normally closed.

4. A combinatorial drug delivery device as in claim 3, wherein, with connection to the further module, the secondary branch line is grounded causing the gate of the MOSFET to open.

5. A combinatorial drug delivery device as in claim 1, further comprising a second digital logic line configured to select the input channels, wherein, with the modules being serially connected, the second digital logic lines are connected in series between the modules with the serially connected second logic lines being connected to the master controller, wherein, the master controller, using selectively the first and second digital logic lines, selects, in sequence, the same identified input channels across all of the modules with measuring a reference voltage across all of the modules for each of the same identified input channels.

* * * * *